United States Patent
Jiang et al.

(10) Patent No.: US 8,140,162 B1
(45) Date of Patent: Mar. 20, 2012

(54) LOW TEMPERATURE DEGRADATION RESISTANT YTTRIA STABILIZED ZIRCONIA

(75) Inventors: Guangqiang Jiang, Santa Clarita, CA (US); Kate E. Purnell, Valencia, CA (US); Gary D. Schnittgrund, Granada Hills, CA (US)

(73) Assignee: Alfred E. Mann Foundation For Scientific Research, Santa Clarita, CA (US)

( * ) Notice: Subject to any disclaimer, the term of this patent is extended or adjusted under 35 U.S.C. 154(b) by 276 days.

(21) Appl. No.: 12/390,782

(22) Filed: Feb. 23, 2009

Related U.S. Application Data

(62) Division of application No. 10/629,291, filed on Jul. 28, 2003, now Pat. No. 7,519,419.

(60) Provisional application No. 60/453,682, filed on Mar. 10, 2003.

(51) Int. Cl.
*A61N 1/375* (2006.01)

(52) U.S. Cl. .......................................... 607/36; 501/105

(58) Field of Classification Search .................... 607/36; 428/697, 701, 702; 501/103, 105, 107
See application file for complete search history.

(56) References Cited

U.S. PATENT DOCUMENTS

| | | | | |
|---|---|---|---|---|
| 5,688,731 A | * | 11/1997 | Chatterjee et al. | 501/96.3 |
| 6,011,993 A | * | 1/2000 | Tziviskos et al. | 607/36 |
| 6,735,475 B1 | * | 5/2004 | Whitehurst et al. | 607/46 |
| 6,931,283 B1 | * | 8/2005 | Magnusson | 607/36 |

* cited by examiner

*Primary Examiner* — Carl H Layno
*Assistant Examiner* — Brian T Gedeon
(74) *Attorney, Agent, or Firm* — Gary D. Schnittgrund

(57) ABSTRACT

The invention is directed to an apparatus substantially eliminating destructive low-temperature, humidity-enhanced phase transformation of yttria-stabilized zirconia in general, as well as eliminating low-temperature degradation of yttria-stabilized tetragonal zirconia polycrystalline ceramic (Y-TZP). The martensitic-type phase transformation from tetragonal to monoclinic is accompanied by severe strength degradation in a moist environment at low-temperature, specifically at room temperature as well as at body temperature. This class of materials has been chosen as the packaging material for small implantable neural-muscular sensors and stimulators because of the high fracture toughness and high mechanical strength. This destructive phase transformation has been substantially eliminated, thus ensuring the safety of long-term implants, by subjecting the sintered components to post-machining hot isostatic pressing, such that the average grain size is less than about 0.5 microns.

16 Claims, 2 Drawing Sheets

LOW TEMPERATURE DEGRADATION RESISTANT YTTRIA STABILIZED ZIRCONIA

CROSS REFERENCE TO RELATED APPLICATION

This application is a divisional of U.S. patent application Ser. No. 10/629,291, now U.S. Pat. No. 7,519,419, filed Jul. 28, 2003; which claims the benefit of U.S. Provisional Application No. 60/453,682, filed on Mar. 10, 2003.

BACKGROUND OF THE INVENTION

A widely employed bioceramic is alumina, which is classed as bioinert. The search for an ideal bioceramic has included alumina, hydroxyapatite, calcium phosphate, and other ceramics. The first use of aluminas for implants in orthopedics and dentistry was in the 1960's and they were employed in hip prostheses as early as 1970. Since those early days the quality and performance of aluminas have improved and high-purity, high-density, fine-grained aluminas are currently used for a wide range of medical applications, e.g. dental implants, middle ear implants, and hip or knee prostheses.

Although the aluminas currently available perform satisfactorily, a further improvement in strength and toughness would increase the safety factor and may extend usage to higher stressed components. A proposed candidate to add to this list is stabilized-zirconia because of its potential advantage over alumina of a lower Young's modulus, higher strength, and higher fracture toughness. Another advantage of stabilized-zirconia is low-wear residue and low coefficient of friction. Zirconia undergoes a destructive phase change at 1000° to 1100° C. from monoclinic to tetragonal, which necessitates phase stabilization by calcia, magnesia, ceria, or yttria.

Tetragonal zirconia polycrystalline ceramic, commonly known as TZP, which typically contains 3 mole percent yttria, coupled with the small size of the particles, results in the metastable tetragonal state at room temperature. Under the action of a stress field in the vicinity of a crack, the metastable particles transform, with a 3% to 4% volume increase, by a shear-type reaction, to the monoclinic phase. Crack propagation is retarded by the transforming particles at the crack tip and by the compressive back stress on the crack walls behind the tip, due to volume expansion associated with transformation to the monoclinic phase.

The well-known transformation toughening mechanism is operative in zirconia ceramics whose composition and production are optimized such that most of the grains have the tetragonal crystal structure. These zirconias are referred to as tetragonal zirconia polycrystal (TZP) ceramics and their mechanical properties in air at room temperature are superior to those of zirconia-toughened aluminas and to other classes of zirconias. To the knowledge of the inventors, the biocompatibility of TZPs has not been fully assessed. However, the biocompatibility of the TZP has been at least preliminarily investigated.

For example, in one study by Thompson and Rawings [see I. Thompson and R. D. Rawlings, "Mechanical Behavior of Zirconia and Zirconia-Toughened Alumina in a Simulated Body Environment," Biomaterials, 11 [7] 505-08 (1990)]. The results that TZP demonstrated a significant strength decrement when aged for long periods in Ringer's solution and was therefore unsuitable as implant material.

Drummond [see J. L. Drummond, J. Amer. Ceram. Soc., 72 [4] 675-76 (1989)] reported that yttria-stabilized zirconia demonstrated low-temperature degradation at 37° C. with a significant decrement in strength in as short as period as 140 to 302 days in deionized water, saline, or Ringer's solution. He also reports on similar observation by others, where yttria-doped zirconia demonstrated a strength decrement in water vapor, room temperature water, Ringer's solution, hot water, boiling water, and post-in vivo aging.

TZP components suffer a decrement in strength properties after exposure for only a few days to humid environments. This degradation of mechanical properties occurs when moisture is present in any form, for example, as humidity or as a soaking solution for the TZP component. TZP components have been observed to spontaneously fall apart after times as short as a few weeks in room temperature water. This is of particular importance in living-tissue implanted devices that contain components made of this class of material. Successful long-term implantation of devices that contain yttria-stabilized zirconia components is not feasible.

DETAILED DESCRIPTION OF THE PREFERRED EMBODIMENT

A broadly applicable material and method of producing the improved material has been developed. It has been demonstrated that hot isostatic pressing a sintered yttria-stabilized tetragonal zirconia polycrystalline ceramic (Y-TZP) dramatically reduces the destructive phase transformation from tetragonal to monoclinic. While this material and the method of production are widely applicable, a preferred embodiment is to apply this invention to implantable devices that are suitable for use as implants in living tissue, an application previously prohibited to this class of ceramic material.

A novel ceramic to metal brazed case has been designed for implantable microstimulator, such as the microstimulator of Advanced Bionics Corporation, 12740 San Fernando Road, Sylmar, Calif. U.S. Pat. Nos. 5,193,540 and 5,324,316 present developments related to this microstimulator and are incorporated in their entirety by reference herein. Yttria stabilized-TZP (Y-TZP) has been selected as the ceramic material because of its high strength, favorable fracture toughness, and biocompatibility. It provides a hermetic and robust housing for the electronic module located inside.

The strength decrement in humid environment varies among Y-TZP ceramics, depending upon the quality of the ceramic and its composition. This variability is related to the differences in equilibrium of microstructural parameters such as: concentration and distribution of phase stabilizer, grain size, flaw population and distribution, residual stress, density, etc.

Figure 1:
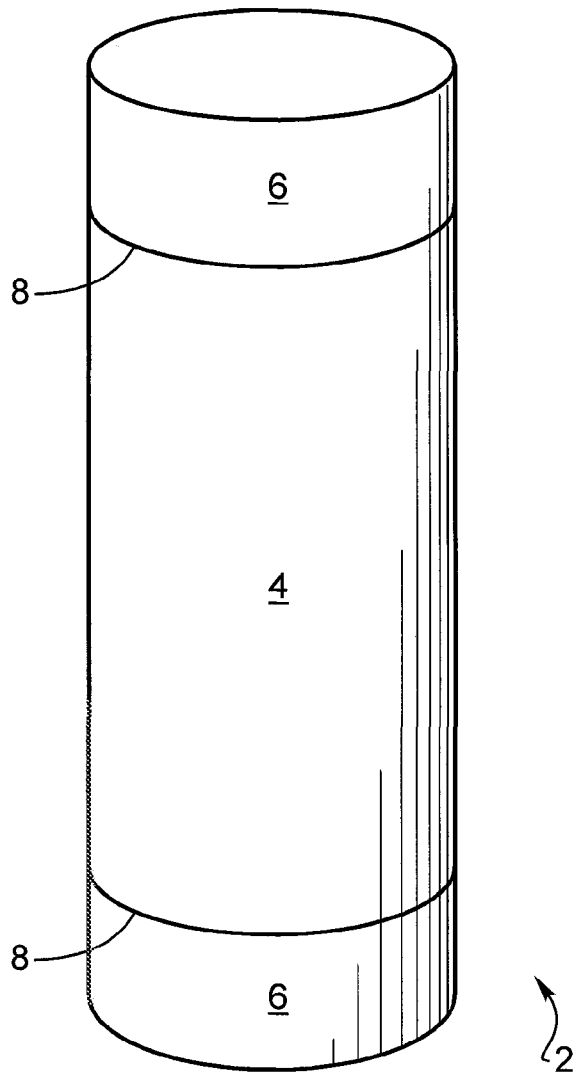
FIG. 1 presents the microstimulator.

A preferred microstimulator 2 is presented in FIG. 1, wherein a hollow ceramic tube 4 is preferably attached by brazing to an electrode 6 on either end of the microstimulator 2, thereby forming a hermetically sealed hollow enclosure suitable to contain electronics for either sensing or stimulating living tissue into which the microstimulator 2 may be implanted. The size of the microstimulator 2 is preferably approximately 10 mm or less in diameter and 100 mm or less in length, preferably less than 6 mm in diameter and 60 mm in length, and of longitudinal shape capable of implantation in the immediate vicinity of selected areas of the body by expulsion through a hypodermic needle or other implantation device.

The ceramic tube 4 is comprised of a strong, hermetic material that is biocompatible, such as Y-TZP. In alternative embodiments, other stabilizer materials may be utilized in place of yttria, such as ceria, magnesia, calcia, hafnia, or other known stabilizing additives.

Figure 2:
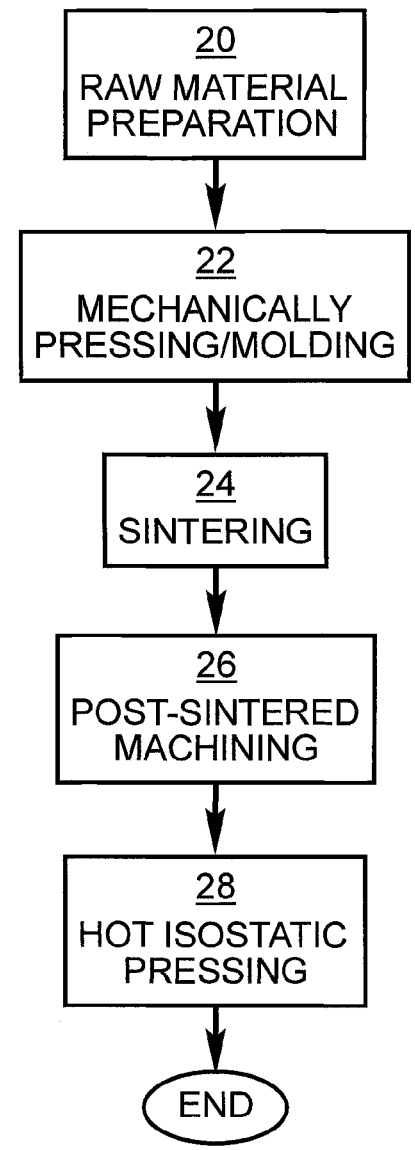
FIG. 2 presents the ceramic processing method steps to form the improved material.

The Y-TZP ceramic tube 4 is formed by conventional ceramic forming processes as shown in FIG. 2, preferably including pressing 22 and sintering 24. The method of forming the tube includes raw material preparation 20, which includes particle size control and binder selection and introduction, as well as selecting the yttria powder and stabilizer. Post-sintering the dense ceramic is optionally machined 26 to final dimensions and required surface finish. The ceramic tube 4 is next further processed by hot isostatic pressing (HIPping) 28 or other known densification methods.

Figure 3:
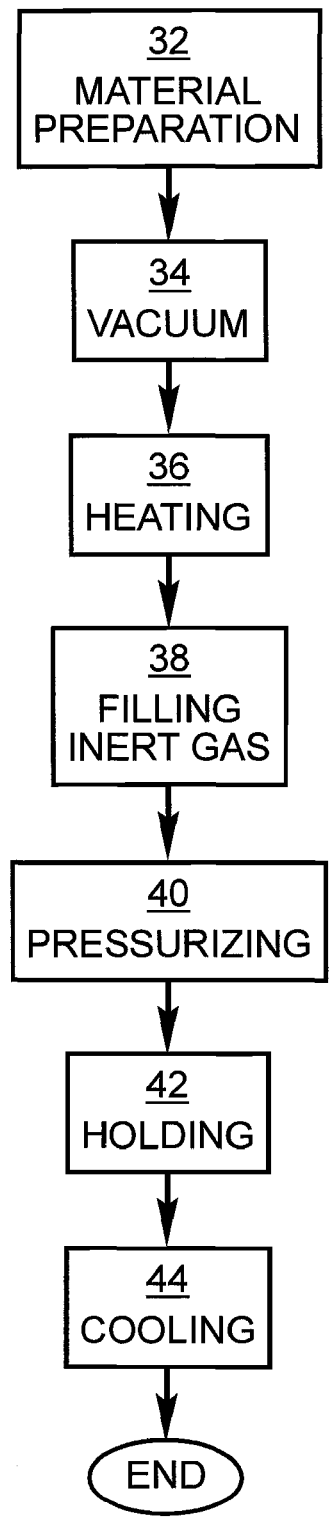
FIG. 3 presents the hot isostatic pressing method steps.

The dense formed ceramic tube 4 is processed according to FIG. 3, where the part is processed 32 by cleaning and is placed in a vacuum 34. The ceramic tube 4 is then heated 36 to 1200° C. to 1450° C. and inert gas is placed in the chamber. It is preferred that argon be used, although other inert gasses may also be selected, as well as selecting a mixture of an inert gas and oxygen, preferably 80 volume percent argon and 20 volume percent oxygen. The chamber is pressurized 40 to preferably approximately 100 MPa, although higher pressures may be utilized to achieve optimum materials properties, and the part is held at temperature and pressure for approximately 30 minutes, although shorter or longer hold times may alternatively be used depending on the selected temperature and pressure. The process chamber and ceramic tube 4 are cooled 44 and the tube 4 is removed and is ready for assembly into the microstimulator 2.

The finished ceramic tube 4 has been post-processed examined to assure that the low-temperature phase transformation has been controlled. Sealed empty brazed cases were used in the in vitro accelerated aging test. Aging treatments were carried out in temperature-controlled ovens and in autoclaves. Low-temperature ceramic degradation was quantified by determining the monoclinic volume fraction ($X_m$) on the ceramic surface of the finished ceramic tube 4. $X_m$ was measured using an X-ray diffraction (XRD) technique and its volume content was calculated from the modified Garvie-Nicholson equation, i.e., $X_m=I_m/(I_m+I_t)$, where $I_m$ is the area under the peak curve for monoclinic phase zirconia as measured by XRD techniques and $I_t$ is the area under the peak curve for tetragonal phase zirconia.

Example 1

As-sintered ceramic tubes having a length of 11.7 mm, an outside diameter 2.3 mm and a wall thickness of 0.5 mm and hot isostatically pressed (HIPped) ceramic tubes having the same size and made in the same batch were soaked in 127° C. steam. X-Ray Diffraction was used to measure the surface monoclinic phase and the monoclinic volume fraction was calculated from the modified Garvie-Nicholson equation.

After soaking in 127° C. steam for 171 hours, the monoclinic content on the surface of as-sintered ceramic tubes reached 35% from its original monoclinic content of 2.0%. After the same period of time soaked in the same environment, the monoclinic content on the HIPped ceramic tubes reaches 22% from 0.6% prior to soaking.

XRD analysis showed that although both HIPped and as-sintered ceramics are subject to moisture-induced tetragonal to monoclinic phase transformation, the transformation rate in HIPped TZP was significantly slower than that demonstrated by non-HIPped TZP.

The HIPping process virtually eliminated porosity of the sintered material, improving flexural strength and fracture toughness. The HIPping operation enhanced the aging resistance. The HIPped Y-TZP is much denser than the as-sintered TZP material, with measured bulk density of about 6.05 g/cm$^3$, compared to the specific gravity of 6.10.

As an additional post-HIPped process, the ceramic tube may be loaded in a flexural bending mode so as to pre-load the tube at a known stress. The stress for this proof test type of qualification is preferably 800 MPa, although higher or lower stresses may be used to either change the acceptance rate or to assure a different minimum failure strength. Because of the small size of the tube, three-point bending is utilized to pre-load the tube, although four-point bending would preferably be used with a longer sample. Tubes that fail to survive the pre-load are thus culled from the sample population thereby giving a minimum strength for the survivors.

Obviously, many modifications and variations of the present invention are possible in light of the above teachings. It is therefore to be understood that, within the scope of the appended claims, the invention may be practiced otherwise than as specifically described.

What is claimed is:
1. A long-lived, stabilized tetragonal zirconia polycrystal ceramic, prepared by the process comprising the steps of:
   hot isostatic pressing said ceramic at a controlled temperature, at a controlled pressure, and in a controlled atmosphere to achieve an average grain size of less than about 0.5 micron, to substantially eliminate open porosity and to increase bulk density to about 100% of theoretical, thereby substantially eliminating low-temperature degradation of said polycrystal ceramic; and
   providing said ceramic as an implantable hollow tube.
2. The ceramic of claim 1, wherein said pressure exceeds 100 MPa for said controlled time of at least 30 minutes in said gas environment of argon gas at said temperature of 1200° to 1450° C.
3. The ceramic of claim 1, wherein said stabilized tetragonal zirconia polycrystal ceramic is yttria stabilized.
4. The ceramic of claim 1, wherein said stabilized tetragonal zirconia polycrystal ceramic is comprised of 3 mole percent yttria stabilized.
5. The ceramic of claim 1, wherein said ceramic has a length less than 100 mm, an outside diameter less than 10 mm and a wall thickness less than 2 mm.
6. The ceramic of claim 1, wherein said ceramic has an outer surface, said surface polished to a surface finish of less than 32 microinch roughness.
7. An implantable ceramic hermetic sealed case which resists low-temperature degradation in living tissue, said case comprised of:
   yttria stabilized tetragonal zirconia polycrystal ceramic;
   a ceramic hollow tube having an average grain size of less than about 0.5 microns;
   a hot isostatic pressed sintered ceramic that has been processed at a known pressure in an inert gas environment for a controlled time in a controlled temperature to eliminate open porosity and to increase bulk density to about 100% of theoretical; and
   said case further comprised of metal end caps that are brazed to said ceramic hollow tube to form said hermetic sealed case.

8. The implantable case of claim 7, wherein said pressure exceeds 100 MPa for said controlled time of at least 30 minutes in said gas environment of argon gas at said temperature of 1200° to 1450° C.

9. The implantable case of claim 7, wherein said stabilized tetragonal zirconia polycrystal ceramic is comprised of 3 mole percent yttria stabilized.

10. The implantable case of claim 7, wherein said implantable case has a length less than 100 mm, an outside diameter less than 10 mm and a wall thickness less than 2 mm.

11. The implantable case of claim 7, wherein said implantable case has an outer surface, said surface polished to a surface finish of less than 32 microinch roughness.

12. An implantable ceramic hermetic sealed case comprised of:
   a hermetically sealed case having an outer surface being inert to body fluids;
   said microstimulator being approximately 10 mm in diameter and 100 mm in length and of longitudinal shape capable of implantation in the immediate vicinity of selected areas of the body by expulsion through a hypodermic needle;
   said case comprised of stabilized tetragonal zirconia polycrystal ceramic;
   said case further comprised of metal end caps that are brazed to said ceramic;
   said case comprised of a sintered ceramic; wherein
   said case is further comprised of a hot isostatic pressed ceramic outer surface that has been pressed at a controlled pressure in a controlled gas at a controlled temperature for a controlled time.

13. The implantable case of claim 12, wherein said pressure exceeds 100 MPa for said controlled time of at least 30 minutes in said gas environment of argon gas at said temperature of 1200° to 1450° C.

14. The implantable case of claim 12, wherein said stabilized tetragonal zirconia polycrystal ceramic is yttria stabilized.

15. The implantable case of claim 12, wherein said stabilized tetragonal zirconia polycrystal ceramic is comprised of 3 mole percent yttria stabilized.

16. The implantable case of claim 12, wherein said implantable case has an outer surface, said surface polished to a surface finish of less than 32 microinch roughness.

* * * * *